United States Patent
Choi et al.

(10) Patent No.: US 7,714,049 B2
(45) Date of Patent: May 11, 2010

(54) COMPOUNDING AGENT FOR RUBBER VULCANIZATION CONTAINING AMINE SALT COMPOUND OF CARBOXYLIC GROUP-CONTAINING DISULFIDE, METHOD FOR PRODUCING THE SAME, RUBBER COMPOSITION CONTAINING THE SAME AND PNEUMATIC TIRE USING THE SAME AS RUBBER FOR BELT COAT AND/OR BELT EDGE CUSH

(75) Inventors: Wonmun Choi, Hiratsuka (JP); Yuuki Shimizu, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 12/377,492

(22) PCT Filed: Aug. 9, 2007

(86) PCT No.: PCT/JP2007/065927

§ 371 (c)(1),
(2), (4) Date: Feb. 13, 2009

(87) PCT Pub. No.: WO2008/020604

PCT Pub. Date: Feb. 21, 2008

(65) Prior Publication Data

US 2010/0004380 A1    Jan. 7, 2010

(30) Foreign Application Priority Data

| Aug. 14, 2006 | (JP) | 2006-221258 |
| Aug. 23, 2006 | (JP) | 2006-227129 |
| Aug. 30, 2006 | (WO) | PCT/JP2006/317590 |
| Aug. 6, 2007 | (JP) | 2007-204681 |

(51) Int. Cl.
   *B32B 7/12* (2006.01)

(52) U.S. Cl. ............ 524/186; 524/303; 562/2; 562/462

(58) Field of Classification Search ............ 524/186, 524/303; 562/2, 462
See application file for complete search history.

(56) References Cited

U.S. PATENT DOCUMENTS 5,274,184 A * 12/1993 Nagl et al. ............ 562/429

FOREIGN PATENT DOCUMENTS

| JP | 63284294 | 11/1988 |
| JP | 04264063 | 9/1992 |
| JP | 6501566 | 2/1994 |
| JP | 9262318 | 10/1997 |
| JP | 200189440 | 4/2001 |
| JP | 2006097024 | 4/2006 |

* cited by examiner

*Primary Examiner*—Peter D Mulcahy
(74) *Attorney, Agent, or Firm*—Connolly Bove Lodge & Hutz LLP

(57) ABSTRACT

A compounding agent for rubber vulcanization comprising an amine salt compound of a carboxylic acid group-containing disulfide having the formula (I):

Figure 1:
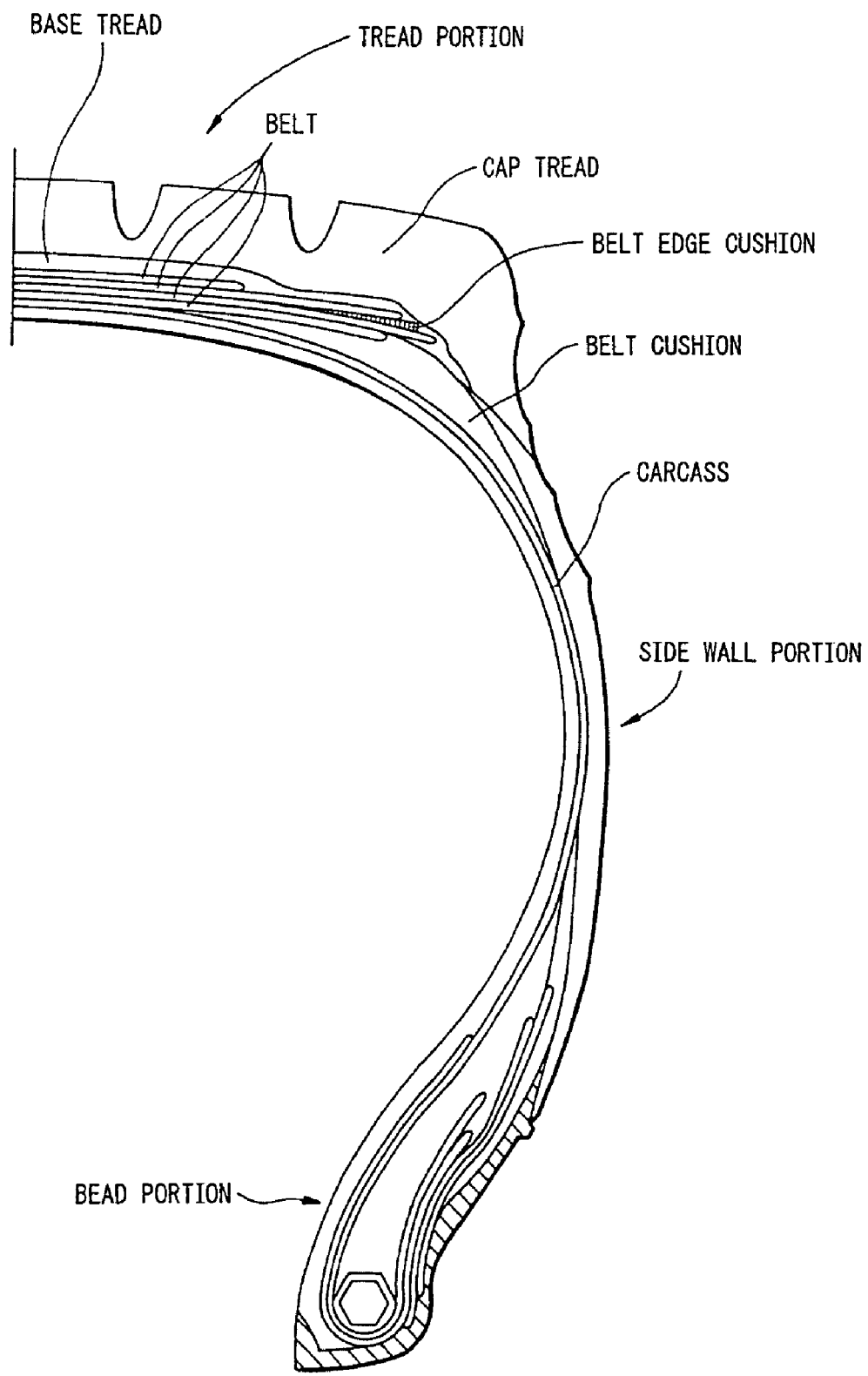

$$R_1 - \overset{\overset{R_2}{|}}{\underset{\underset{H}{|}}{N^+}} - R_3 \quad\quad R_1 - \overset{\overset{R_2}{|}}{\underset{\underset{H}{|}}{N^+}} - R_3$$

$${}^-OOC - X - S - S - X - COO^-$$

wherein $R_1$, $R_2$ and $R_3$ are independently hydrogen or a $C_1$-$C_{20}$ organic group which may have a heteroatom and/or a substituent group, and X is a $C_2$-$C_{20}$ organic group which may have a heteroatom and/or a substituent group, a method for producing the same and a rubber composition containing the same, capable of improving the vulcanization rate and vulcanized rubber physical properties, without having a detrimental effect on the scorch time.

9 Claims, 1 Drawing Sheet

COMPOUNDING AGENT FOR RUBBER VULCANIZATION CONTAINING AMINE SALT COMPOUND OF CARBOXYLIC GROUP-CONTAINING DISULFIDE, METHOD FOR PRODUCING THE SAME, RUBBER COMPOSITION CONTAINING THE SAME AND PNEUMATIC TIRE USING THE SAME AS RUBBER FOR BELT COAT AND/OR BELT EDGE CUSH

CROSS REFERENCE TO RELATED APPLICATIONS

This application is a National Stage of PCT/JP2007/065 927 filed Aug. 9, 2007 which in turn claims priority from Japanese Application 2006-221258 filed Aug. 14, 2006, Japanese Application 2006-227129 filed Aug. 23, 2006, International Application PCT/JP2006/3 17590 filed Aug. 30, 2006 and Japanese Application 2007-20498 1 filed Aug. 6, 2007, the entire contents of which are incorporated herein by reference.

TECHNICAL FIELD

The present invention relates to a novel compounding agent for rubber vulcanization containing an amine salt compound of a carboxylic acid group-containing disulfide (hereinafter sometimes referred to simply as an "amine salt of disulfide") and a method for producing the same and a rubber composition containing the same. The present invention further relates to a rubber composition for a tire and a pneumatic tire using the same, more particularly relates to a rubber composition for a tire having an improved bonding performance with a metal belt and low heat buildup property and a pneumatic tire using the same as a rubber for a belt coat and/or belt edge cushion.

BACKGROUND ART

In general, as a vulcanization accelerator of rubber, a thiuram-based, sulfonamide-based, mercaptobenzothiazole-based or other accelerators are used. A sulfonamide-based vulcanization accelerator is a delayed action type accelerator, which is believed to produce mercaptobenzothiazole and amine by dissociation of the N—S bonds by heat during vulcanization. It is known that the produced mercaptobenzothiazole acts as a vulcanization accelerator, while the amine plays an important role in accelerating the vulcanization reaction by coordinating with zinc oxide to activate the vulcanization system and by reaction with the vulcanization intermediate (see Non-Patent Document 1).

As opposed to this, the disulfide-based vulcanization agent, dibenzothiazole disulfide, produces mercaptobenzothiazole by dissociation of the S—S bonds due to heat, but has no ability to stimulate the vulcanization by amines, and therefore, it is reported to vulcanization is slow and vulcanization accelerating capability is inferior to sulfenamides. It may be considered to jointly use amines for the purpose of improving the vulcanization accelerating ability of dibenzothiazole disulfide, but in such a case, since the reactivity of the free amines is high, there is the problem that they would react with the sulfur and other vulcanization agents even at a low temperature whereby a detrimental effect on the scorch time occurs.

Further, Patent Documents 1 to 6 describe various types of amine salts of carboxylic acid disulfides, but these documents described examples of using a quaternary ammonium salt of a carboxylic acid group-containing disulfide as a static electricity suppressant for a color toner for electrostatic charged image development (Patent Document 1), using a disulfide-containing amine salt as an aqueous ink composition for a ball point pen (Patent Document 2), using a mono- or di-amine salt of a dithiodipropionic acid or dithiodiglycolic acid as a rust preventing agent (Patent Document 3), a method for producing a quaternary ammonium salt of a carboxylic acid group-containing disulfide (Patent Document 4), using a quaternary ammonium salt of a carboxylic acid-containing disulfide as a toner for electronic photograph recording and a charge suppresser for a developer (Patent Document 5), and using a 3-mercaptopropionic acid disulfide as a water-soluble additive for a water-soluble functional fluid (Patent Document 6), but the art of introducing these salt compounds as a rubber vulcanization use compounding agent was not known. In particular, in the case of the quaternary ammonium salt of a carboxylic acid group-containing disulfide used in Patent Documents 1 and 4, since the amine ingredient acting to accelerate the vulcanization reaction is a quaternary amine, no substantial role of accelerating the vulcanization reaction can be expected.

Further, Patent Documents 7 and 8 disclose using a carboxyl group-containing disulfide as a vulcanization agent for rubber, but these are both carboxylic acid-containing disulfide compounds and not salt compounds containing an amine component having the role of accelerating the vulcanization reaction.

Further, a method for producing an amine salt of a polythiopolycarboxylic acid having 2 to 14 sulfur atoms is described in Patent Document 9. Patent Document 9describes, as prior art, European Patent Publication EP-A-0,780,429 (Patent Document 10) describing a method for producing di-, tri- and tetra-thiodipropionic acids. This production method has the defects that the content of the bonded sulfur is narrowly limited. Mixtures containing about 70% of dithiodipropionic acid and only about 30% of tri- and tetra-thiodipropionic acids are produced. As opposed to this, Patent Document 9 discloses a method for producing particularly pure polythiopolycarboxylic acid which enables the production of a compound containing a relatively high content of bonded sulfur. The examples of Patent Document 9 also disclose methods for producing polythiodipropionic acids having averages of four sulfur atoms and 3 to 11 sulfur atoms.

In general, sulfur compounds are classified by the number of sulfur atoms into mono- (one sulfur atom), di-(two sulfur atoms) and poly- (three or more sulfur atoms) sulfide compounds. This is because the dissociation energy of the sulfur bonds is about 70 kcal/mol in the case of disulfide and 45 kcal/mol in the case of trisulfide (three sulfur atoms) and, therefore, greatly differs according to the number of sulfur atoms and, when the number of sulfur atoms becomes 3 or more, the sulfur bonds easily dissociate (see Non-Patent Document 1). Therefore, a polysulfide compound is inferior to a disulfide compound in the heat stability, and, therefore, has the problem that it easily reacts with sulfur and other vulcanization agents or rubber etc. even at a low temperature and provides a detrimental effect on the processing process such as scorching of the rubber during mixing and shortening of the scorch time.

The bonding performance of the metal belt and rubber in a pneumatic tire is, of course, important from the viewpoint of the tire being a composite material. If this bonding performance is low, it leads to tire separation or other trouble. As a measure against this, the introduction of cobalt (Co) salts and changes in the vulcanization accelerator to make the bonding reaction better have been attempted (see Non-Patent Document 2), but this has the problem of a deterioration in the heat buildup property.

Non-Patent Document 1: Chapman, A. V., Porter, M.: "Sulphur Vulcanization Chemistry" in *Natural Rubber Science and Technology*, Roberts, A. D. Ed., Oxford Science Publications, London (1988).

Non-Patent Document 2: *Journal of the Society of Rubber Industry of Japan*, vol. 65, page 70 (1992)

Patent Document 1: Japanese Patent Publication (A) No. 2004-354708

Patent Document 2: Japanese Patent Publication (A) No. 2004-115684

Patent Document 3: Japanese Patent Publication (A) No. 11-92979

Patent Document 4: Japanese Patent Publication (A) No. 4-264063

Patent Document 5: Japanese Patent Publication (A) No. 6-501566

Patent Document 6: Japanese Patent Publication (A) No. 63-284294

Patent Document 7: Japanese Patent Publication (A) No. 2002-224244

Patent Document 8: Japanese Patent Publication (A) No. 9-262318

Patent Document 9: Japanese Patent Publication (A) No. 2001-89440

Patent Document 10: European Patent Publication EP-A-0.780, 429

DISCLOSURE OF INVENTION

Accordingly, the object of the present invention is to provide a use compounding agent for rubber vulcanization containing an amine salt compound of a carboxylic acid group-containing disulfide capable of improving the vulcanization speed and vulcanized rubber physical properties, without detrimentally affecting the scorch time, a method for producing the same and a rubber composition containing the same.

Another object of the present invention is to provide a rubber composition having improved bonding performance with a metal belt and low heat buildup property suitable for use as a rubber for belt coat and/or belt edge cushion etc. of a pneumatic tire, containing an amine salt compound of a carboxylic acid group-containing disulfide as a compounding agent for rubber vulcanization, and a pneumatic tire using the same.

In accordance with the present invention, there is provided a compounding agent for rubber vulcanization comprising an amine salt compound of a carboxylic acid group-containing disulfide having the formula (I): formula (I):

$$R_1 \overset{R_2}{\underset{H}{\overset{+}{N}}} R_3 \quad\quad R_1 \overset{R_2}{\underset{H}{\overset{+}{N}}} R_3 \quad (I)$$
$$^-OOC-X-S-S-X-COO^-$$

wherein $R_1$, $R_2$ and $R_3$ are independently hydrogen or a $C_1$ to $C_{20}$ organic group which may have a heteroatom and/or a substituent group and X is $C_2$-$C_{20}$ organic group which may have a heteroatom and/or a substituent group.

In accordance with the present invention, there is provided a compounding agent for rubber vulcanization comprising an amine salt compound of a carboxylic acid group-containing disulfide having by the formula (I), wherein, in the above formula (I), the amine component is a primary or secondary amine.

In accordance with the present invention, there is provided a compounding agent for rubber vulcanization containing an amine salt compound of a carboxylic acid group-containing disulfide having the formula (I) wherein, in the above formula (I), X is an aromatic group.

In accordance with the present invention, there is further provided a method for producing a compounding agent for rubber vulcanization containing an amine salt compound of a carboxylic acid group-containing disulfide having the formula (I) comprising:

reacting a disulfide compound containing a carboxylic acid group having the formula (II) and an amine having the formula (III) (see the following reaction formula (1)).

Reaction formula (1)

$$HOOC-X-S-S-X-COOH \;+\; \underset{(III)}{\overset{R_1}{\underset{R_3}{\overset{|}{N}}}-R_2} \longrightarrow$$

$$R_1 \overset{R_2}{\underset{H}{\overset{+}{N}}} R_3 \quad\quad R_1 \overset{R_2}{\underset{H}{\overset{+}{N}}} R_3$$
$$^-OOC-X-S-S-X-COO^-$$
(I)

wherein $R_1$, $R_2$ and $R_3$ are independently hydrogen or a $C_1$-$C_{20}$ organic group which may have a heteroatom and/or a substituent group and X is a $C_2$-$C_{20}$ organic group which may have a heteroatom and/or a substituent group.

In accordance with the present invention, there is provided a method for producing a compounding agent for rubber vulcanization containing an amine salt compound of a carboxylic acid group-containing disulfide having the formula (I) comprising:

reacting a thiol compound having a carboxylic acid group expressed by the formula (IV) and an amine having the formula (III) in the presence of an oxidizing agent (see the following reaction formula (2)).

Reaction formula (2)

$$HOOC-X-SH \;+\; \underset{(III)}{\overset{R_1}{\underset{R_3}{\overset{|}{N}}}-R_2} \longrightarrow$$
(IV)

$$R_1 \overset{R_2}{\underset{H}{\overset{+}{N}}} R_3 \quad\quad R_1 \overset{R_2}{\underset{H}{\overset{+}{N}}} R_3$$
$$^-OOC-X-S-S-X-COO^-$$
(I)

wherein $R_1$, $R_2$ and $R_3$ are independently hydrogen or a $C_1$-$C_{20}$ organic group which may have a heteroatom and/or a substituent group and X is a $C_2$-$C_{20}$ organic group which may have a heteroatom and/or a substituent group.

In accordance with the present invention, there are further provided a rubber composition for a tire comprising (A) 100 parts by weight of a diene-based rubber containing at least 30 parts by weight of a natural rubber (NR) and/or polyisoprene rubber (IR), (B) 0.1 to 5 parts by weight of an amine salt compound of a carboxylic acid group-containing disulfide having the formula (I)

(C) 20 to 80 parts by weight of carbon black having an iodine adsorption of 70 to 140 g/kg and a DBP absorption of 60 to $180 \times 10^{-5}$ m$^3$/kg and (D) 0.05 to 0.5 parts by weight, in terms of a metal content, of an organic metal salt and a pneumatic tire using the same as a rubber for a belt coat and/or belt edge cushion.

In accordance with the present invention, by using an amine salt of a disulfide having the formula (I), it is possible to obtain a high vulcanization acceleration effect for a diene-based rubber, halogenated butyl rubber, etc. and further possible to improve the vulcanization speed and vulcanized rubber physical properties (e.g., the heat aging resistance), without detrimentally affecting the scorch time.

In accordance with the present invention, further, by blending in the amine salt compound of a carboxylic acid-containing disulfide as a vulcanization accelerator into a rubber composition, it is possible to achieve both an improvement in the bonding performance of a pneumatic tire with a metal belt and the low heat buildup property.

BRIEF DESCRIPTION OF THE INVENTION

FIG. 1 is a cross-sectional view along the meridian of a typical pneumatic tire showing a belt and/or belt edge cushion using the rubber composition of the present invention together with other parts.

BEST MODE FOR CARRYING OUT THE INVENTION

The amine salt compound of a carboxylic acid group-containing disulfide according to the present invention (i.e., the amine salt of a disulfide of the present invention) is a compound having the formula (I).

In the formula (I), $R_1$, $R_2$ and $R_3$ may be, independently, a hydrogen or a $C_1$ to $C_{20}$, preferably $C_1$ to $C_{12}$, organic group. As the organic group, for example, a methyl group, ethyl group, propyl group, butyl group, hexyl group, stearyl group or other chain type hydrocarbon group or a cyclopropyl group, cyclobutyl group, cyclohexyl group or other cyclic hydrocarbon group may be mentioned. The chains of these organic groups may include a nitrogen atom, oxygen atom, sulfur atom or other heteroatom. As examples of such organic groups, for example, a methoxypropyl group, methoxyethyl group, tetrahydrofurfuryl group, etc. may be mentioned. $R_1$ and $R_2$ may, together with the nitrogen atoms they bond with, form a heterocyclic group, for example, imidazole group, triazole group, pyrazole group, aziridine group, pyrrolidine group, piperidine group, morpholine group, thiomorpholine group or other group. When $R_1$ and $R_2$ form heterocyclic groups, together with the nitrogen atoms with which they bond, they may further have substituent groups on their hetero rings. As examples of the substituent group, methyl, ethyl or other alkyl groups; bromo, chloro or other halogen groups; alkoxyl group, carboxyl group, ester group, etc. may be mentioned.

In the formula (I), X is an organic group selected from a substitutable $C_2$-$C_{20}$, preferably $C_2$-$C_{12}$, chain hydrocarbon group or alicyclic hydrocarbon group, aromatic hydrocarbon group and heterocyclic group. As examples of the organic groups, a methylene group, ethylene group, propylene group, hexylene group, cyclobutylene group, cyclohexylene group, phenylene group, thiazole group, thiadiazole group, pyridilene group, naphthylene group, etc. may be mentioned. When X is a chain hydrocarbon group or alicyclic hydrocarbon group, X may contain, in the carbon chain thereof, a heteroatom selected from the group consisting of a nitrogen atom, oxygen atom and sulfur atom and may have a methyl, ethyl or other alkyl group, bromo, chloro or other halogen group, ether group, ester group, etc., X is preferably a $C_2$-$C_{12}$ chain hydrocarbon group, aromatic group, heterocyclic group or other aromatic group. An aromatic group is more preferable. If X is an aromatic group, an aromatic carboxylic acid has a higher acidity than an aliphatic carboxylic acid, has a higher ability to form salts with amines, and has a stable amine salt formed, and, therefore, it is believed to have less of an adverse effect on scorching, during mixing and low temperature processing of the rubber composition and, therefore, it is preferable.

As amines of the formula (III), primary, secondary or tertiary amines are preferable, in particular primary or secondary amines are more preferable, since they easily form salts with carboxylic acids and have a coordinating ability with zinc oxide and high ability to accelerate vulcanization reactions due to reaction with the vulcanization intermediates etc.

The amine salt compound of disulfide (I) according to the present invention can be produced, as shown in the reaction formula (1), by reacting a disulfide compound having a carboxylic acid group shown in the formula (II), wherein X is as defined above, and an amine of the formula (III), wherein, $R_1$, $R_2$ and $R_3$ are as defined above. This reaction does not require any oxidizing agent, catalyst, etc. The production is possible by mixing and reacting the compounds having the formula (II) and formula (III) in a suitable solvent (e.g., methanol, ethanol, propanol or other aliphatic alcohols, diethyl ether, tetrahydrofuran or other ethers, acetone, 2-butanone or other ketones etc.).

According to another aspect of the present invention, the amine salt compound of disulfide (I) may be produced as shown in the reaction formula (2) by reacting a thiol compound (IV) containing a carboxylic acid in one molecule and an amine (III) in the presence of an oxidizing agent.

In the reaction formulae (1) and (2), the amine (III) is preferably reacted with the carboxylic acid group of the disulfide compound (II) or thiol compound (IV) in excess of the stoichiometric amount (e.g., 1.01 to 1.15 equivalents).

In the reaction formula (1), as specific examples of the carboxylic acid group-containing disulfide compound (II) used as the starting materials, for example, dithiodiglycolic acid, dithiodipropionic acid, dithiosalicylic acid, dithiobis(2-nitrobenzoic acid), etc., may be mentioned. On the other hand, as thiol compounds expressed by the formula (IV) used in the reaction formula (2), mercaptoacetic acid, 2-mercaptopropionic acid, 3-mercaptopropionic acid, thiosalicylic acid, thionicotinic acid, etc. may be mentioned.

On the other hand, as specific examples of the amines having by the above formula (III), for example, methylamine, ethylamine, propylamine, butylamine, hexylamine, isobutylamine, tert-butylamine, dimethylamine, diethylamine, dipropylamine, diisopropylamine, cyclopropylamine, cyclobutylamine, cyclohexylamine, N-methylcyclohexylamine, N-ethylcyclohexylamine, dicyclohexylamine, 2-methylcyclohexylamine, exo-2-aminonorbornane, 2-methoxyethylamine, bis(2-methoxyethyl)amine, tetrafurfurylamine, morpholine, thiomorpholine, 1-methylpiperadine, 2-methylimidazole, piperadine, trimethylamine, triethylamine, tripropylamine, etc. may be mentioned.

The oxidizing agent usable in the reaction formula (2) is not particularly limited, but the following compounds may be mentioned: sodium chlorate, potassium chlorate, ammonium chlorate or other chlorates; sodium perchlorate, potassium perchlorate or other perchlorate; lithium peroxide, sodium peroxide, potassium peroxide or other inorganic peroxides; sodium chlorite, potassium chlorite or other chlorites; sodium bromate, potassium bromate or other bromates; sodium nitrate, potassium nitrate, ammonium nitrate or other nitrates; sodium iodate, potassium iodate, calcium iodate or other iodates; potassium permanganate, sodium permanganate or other permanganates; sodium dichromate, potassium dichromate or other dichromates; sodium periodate and other periodates; metaperiodic acid or other periodic acids; anhydrous chromic acid (chrome trioxide) or other chrome oxides; lead dioxide or other lead oxides; diiodine pentaoxide and other iodine oxides; sodium nitrite, potassium nitrite and other nitrites; calcium hypochlorite or other hypochlorites; trichlorinated isocyanuric acid or other chlorinated isocyanuric acids; ammonium peroxodisulfate or other peroxodisulfates; ammonium peroxoborate or other peroxoborates; perchloric acid; hydrogen peroxide; nitric acid, chlorine fluoride, bromine trifluoride, bromine pentafluoride, iodine pentafluoride, iodine or other halogenated compounds; copper ethylenediamine tetraacetate, copper nitrilotripropionate or other water-soluble chelate compounds of copper; dimethylsulfoxide or other organic compounds; oxygen, etc. When using oxygen as the oxidizing agent, it is also possible to use air as the oxygen source. These may be used alone or may be used in any combination thereof. Among these, from the viewpoint of easy reaction and high efficiency, sodium chlorate, sodium perchlorate, sodium peroxide, sodium chlorite, hydrogen peroxide, iodine, copper ethyleneamine tetraacetate, copper nitrilotripropionate and oxygen are preferable.

As solvents usable for the reaction, methanol, ethanol, propanol, isopropanol, butanol or other aliphatic alcohols, diethyl ether, tetrahydrofuran (THF), isopropyl ether or other ethers, acetone, 2-butanone, or other ketones, acetonitrile, dimethylformamide (DMF) or other nitrogen-containing organic solvents, etc. may be mentioned. These solvent may be used alone or in the form of mixed solvents. Among these, from the viewpoint of the high solubility with respect to disulfides, thiols and amines and the ease of removal of reaction products, aliphatic alcohols, ethers and ketones are preferable.

The reaction temperature of the reaction is not particularly limited, but is preferably a range of 0° C. to 100° C. If less than 0° C., the reaction time becomes longer, while at a temperature of more than 100° C., unpreferable secondary reactions of the products are liable to occur. The reaction temperature is more preferably a range of 20° C. to 70° C.

As specific examples of the vulcanization agent usable in the compounding agent for rubber vulcanization according to the present invention, for example, sulfur, organic peroxide, quinone dioxime, metal oxides, alkylphenol formaldehyde resins, etc. may be mentioned.

As the compounding agent for rubber vulcanization usable, together with the amine salt of a disulfide according to the present invention, a sulfenamide-based or thiuram-based vulcanization accelerator is preferably included. By using a sulfenamide-based or thiuram-based vulcanization accelerator, it is possible to further accelerate the vulcanization of the rubber ingredients and further improve the physical properties of the obtained vulcanized rubber. As sulfenamide-based vulcanization accelerators, for example, N-cyclohexyl-2-benzothiazolyl sulfenamide, N-t-butyl-2-benzothiazolyl sulfenamide, N-oxydiethylene-2-benzothiazolyl sulfenamide and N,N'-dicyclohexyl-2-benzothiazolyl sulfenamide may be mentioned. As thiuram-based vulcanization accelerators, for example, tetrakis(2-ethylhexyl)thiuram disulfide, tetramethylthiuram disulfide, tetraethylthiuram disulfide, tetramethylthiuram monosulfide, tetrabenzylthiuram disulfide, dipentamethylenethiuram tetrasulfide, etc. may be mentioned.

The rubber composition of the present invention includes an unvulcanized rubber component selected from the group consisting of diene-based rubbers and halogenated rubbers and the amine salt of a disulfide (I) according to the present invention. The unvulcanized rubber component which this rubber composition may include is selected from the group consisting of diene-based rubbers and halogenated rubbers. As specific examples of the diene-based rubber, natural rubber, butadiene rubber, isoprene rubber, chloroprene rubber, styrene-butadiene copolymer rubber, ethylene-propylene-diene copolymer rubber and acrylonitrile-butadiene copolymer rubber may be mentioned. Further, as specific examples of halogenated rubber, brominated butyl rubber, chlorinated butyl rubber and other halogenated butyl rubbers, halides of isobutylene-p-methylstyrene copolymers (e.g., bromides), chloroprene rubber, epichlorohydrin rubber, chlorosulfonated polyethylene, chlorinated polyethylene, maleated chlorinated polyethylene, chlorinated acryl rubber, fluororubber, epoxylated acryl rubber, an acryl rubber obtained by copolymerizing a halogen-based monomer, etc. may be mentioned.

In the rubber composition of the present invention, the amine salt of a disulfide (I) according to the present invention may be used, as a compounding agent for rubber vulcanization alone or together with a vulcanization agent or vulcanization accelerator generally used as a vulcanization agent or vulcanization accelerator for unvulcanized rubber in this technical field. The amine salt of a disulfide (I) of the present invention may be used in any ratio based upon the total weight of the other vulcanization agent and/or vulcanization accelerator included in the compounding agent for rubber vulcanization so long as not inhibiting the vulcanization and/or vulcanization accelerating action of the amine salt of a disulfide (I) and capable of achieving the desired vulcanization and/or vulcanization acceleration effect and improvement of the heat aging resistance. However, to achieve the desired vulcanization and/or vulcanization accelerating effect, the amount is preferably 0.1 to 20 parts by weight, based upon 100 parts by weight of the unvulcanized rubber ingredient selected from the group consisting of diene-based rubbers and halogenated rubber. If the amount of the amine salt of the disulfide (I) is in this range, a practical strength and rubber elasticity or other more advantageous effects are obtained. Further, the vulcanization temperature is usually preferably 140° C. to 200° C.

The rubber composition of the present invention may contain, in addition to the above vulcanization accelerator, compounding agents and additives usually compounded into rubber compositions such as carbon black, silica or other reinforcing agents, a vulcanization or cross-linking agent, vulcanization or cross-linking accelerator, stearic acid or zinc oxide and magnesium oxide or other vulcanization accelerators, various types of oils, an antioxidant, filler, paraffin oil or other softening agents, a plasticizer, an antioxidant, etc. in the generally used amounts by the general mixing method according to various types of applications. For this, a general use rubber kneading device, for example, rolls, a Banbury mixer, kneader, etc. may be used.

The inventors engages in research to solve the above-mentioned problem and, as a result, succeeded in achieving both an improvement in the bonding performance of a tire with a metal belt and a low heat buildup property by using an amine salt compound of a carboxylic acid group-containing disulfide, as a vulcanization accelerator, and compounding it in the rubber composition along with the rubber component and a specific carbon black and organic metal salt.

For the rubber component blended into the rubber composition of the present invention as the component (A), natural rubber (NR) and/or polyisoprene rubber (IR) is compounded into 100 parts by weight of the diene-based rubber in an amount of at least 30 parts by weight, preferably 40 to 90 parts by weight. If the amount of the NR and/or IR is small, the strength is insufficient, and, therefore, this is not preferable. As the other diene-based rubber usable in the present invention, any diene-based rubber capable of compounding in a rubber composition for tire can be used. Specifically, butadiene rubber, chloroprene rubber, styrene-butadiene copolymer rubber, ethylene-propylene-diene copolymer rubber, acrylonitrile-butadiene copolymer rubber, etc. may be mentioned.

According to the present invention, the amine salt compound of a carboxylic acid group-containing disulfide having the formula (I) is mixed in an amount of 0.1 to 5 parts by weight, preferably 0.3 to 4.5 parts by weight, based upon 100 parts by weight of the diene-based rubber. If the amount of this amine salt compound of a carboxylic acid group-containing disulfide compound (I) is small, the hardness becomes insufficient, and, therefore, this is not preferable, while conversely if large, the elongation at break becomes insufficient, and, therefore, this is not preferable.

The compounding agent for rubber vulcanization used in the rubber composition of the present invention (hereinafter also referred to as a "vulcanization accelerator") may be comprised of only the amine salt compound of a carboxylic acid group-containing disulfide (I) or may include, in addition to the amine salt compound of a carboxylic acid group-containing disulfide, compounds generally used as vulcanization accelerators of unvulcanized rubber in this technical field. The amine salt compound of a carboxylic acid group-containing disulfide of the present invention can be used in any ratio based upon the total weight of the other vulcanization accelerators so long as not obstructing the vulcanization acceleration action of the amine salt compound of a carboxylic acid group-containing disulfide and the desired vulcanization acceleration effect can be achieved.

The rubber composition of the present invention may jointly use, as another vulcanization accelerator, for example, a sulfenamide-based, thiuram-based or thiazole-based vulcanization accelerator. By using a sulfenamide-based, thiuram-based or thiazole-based vulcanization accelerator, it is possible to further accelerate the vulcanization of the rubber ingredient. As a sulfenamide-based vulcanization accelerator, for example, N-cyclohexyl-2-benzothiaazolyl sulfenamide, N-t-butyl-2-benzothiazolyl sulfenamide, N-oxydiethylene-2-benzothiazolyl sulfenamide, and N,N'-dicyclohexyl-2-benzothiazolyl sulfenamide may be mentioned. As the thiuram-based vulcanization accelerator, for example, tetrakis(2-ethylhexyl)thiuram disulfide, tetramethylthiuram disulfide, tetraethylthiuram disulfide, tetramethylthiuram monosulfide, tetrabenzylthiuram disulfide, and dipentamethylenethiuram tetrasulfide may be mentioned. As a thiazole-based vulcanization accelerator, 2-mercaptobenzothiazole and dibenzothiazyl disulfide may be mentioned.

As specific examples of the vulcanization agent usable in the rubber composition of the present invention, for example, sulfur, organic peroxide, quinone dioxime, metal oxides, alkylphenol formaldehyde resin, etc. may be mentioned.

The rubber composition of the present invention includes, as the component (C), carbon black having an iodine adsorption of 70 to 140 g/kg, preferably 75 to 130 g/kg, and a DBP absorption of 60 to $180 \times 10^{-5}$ m$^3$/kg, preferably 65 to $160 \times 10^{-5}$ m$^3$/kg, in an amount of 20 to 80 parts by weight, preferably 30 to 70 parts by weight, based upon 100 parts by weight of the rubber ingredients (A). If the iodine adsorption of the carbon black is small, measured according to JIS K 6217-1, the strength of the rubber will be insufficient, and, therefore, this is not preferable, while conversely if large, the heat buildup property becomes poorer, and, therefore, this is not preferable. Further, if the DBP absorption of the carbon black, measured according to JIS K 6217-4 is small, the hardness will be insufficient, and, therefore, this is not preferable, while conversely if large, the elongation at break will become insufficient, and, therefore, this is not preferable either.

The rubber composition of the present invention includes, as the component (D), an organic metal salt in a metal content of 0.05 to 0.5 part by weight, preferably 0.1 to 0.4 part by weight, based upon 100 parts by weight of the rubber ingredient (A). If the amount compounded is too small, the bonding performance with the metal belt is insufficient, and, therefore, this is not preferable, while conversely if too large, the fatigue resistance becomes insufficient, and, therefore, this is not preferable. As the organic metal salt usable in the present invention, use of a nickel (Ni) or cobalt (Co) salt is preferable. Specifically, Ni(CH$_7$O$_2$)$_2$·2H$_2$O made by Nihon Kagaku Sangyo (i.e., Ni content 20.04%), cobalt naphthenate made by Nikko Materials (i.e., Co content 10%), Manobond made by Rhodia (i.e., Co content 22%), Co(C$_5$H$_7$O$_2$)$_3$ made by Nihon Kagaku Sangyo (i.e., Co content 16.54%), etc. may be used.

The rubber composition of the present invention may contain, in addition to the above components, silica or another filler, a vulcanization or cross-linking agent, various types of oils, an antioxidant, a plasticizer or other various types of additives generally included for tire use and other rubber composition use. These additives may be kneaded by a general method using a general use rubber kneading device such as rolls, a Banbury mixer, kneader, etc. to obtain a composition for use for vulcanization or cross-linking. The amounts of these additives may be made the conventional general amounts so long as not running counter to the present invention.

The rubber composition of the present invention can be suitably used as a rubber for belt coat and belt edge cushions of the typical pneumatic tire shown schematically in FIG. 1. It can be used as is on conventional general pneumatic tires.

EXAMPLES

The present invention will now be explained in further detail with reference to the Examples and Comparative Examples shown below, but the technical scope of the present invention is not limited to these Examples of course.

Preparation Example 1

Synthesis of Amine Salt Compound of Disulfide A

In methanol 1000 g, dithiosalicyclic acid 306.4 g (1 mol) and cyclohexylamine 218.2 g (2.2 mol) were charged and reacted at room temperature for 30 minutes. After the reaction ended, the methanol was removed in vacuo. The product was filtered and washed with acetone two times and dried to obtain a white powder compound A having the following formula in 499.2 g (yield 99%).

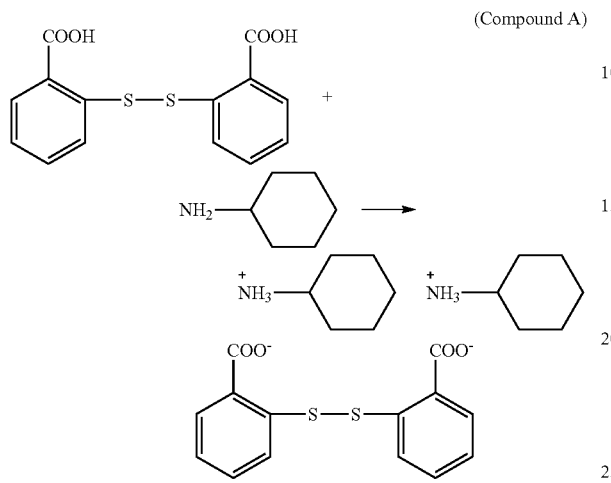

(Compound A)

$^1$HNMR (400 MHz, DMSO-$d_6$) δ in ppm: 1.0-1.3, 1.5, 1.7, 1.9, 2.9, 7.1, 7.2, 7.5, 7.8 Elementary analysis value (%): $C_{26}H_{36}N_2O_4S_2$ Calculated: C, 61.87; H, 7.19; N, 5.55; S, 12.71. Found: C, 61.54; H, 7.28; N, 5.56; S, 12.72.

Preparation Example 2

Synthesis of Amine Salt Compound of Disulfide B

Thiosalicyclic acid 308.4 g (2 mol) and cyclohexyl amine 218.2 g (2.2 mol) were charged into isopropyl alcohol 1000 g together with copper disodium ethylenediamine tetraacetate tetrahydrate 7.5 g (0.8 mol %) and reacted under an oxygen atmosphere at 50° C. for 3 hours. After the reaction ended, the product was filtered and dried to obtain a compound B having the following formula in 479.0 g (yield 95%).

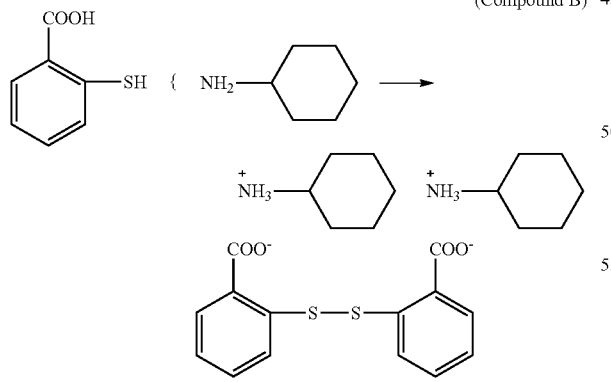

(Compound B)

Preparation Example 3

Synthesis of Amine Salt Compound of Disulfide C 3,3'-dithiopropionic acid 210.3 g (1 mol) and cyclohexyl amine 218.2 g (2.2 mol) were charged in methanol 1000 g and reacted at room temperature for 30 minutes. After the end of the reaction, the methanol was removed in vacuo. The product was filtered and washed with acetone two times and dried to obtain a white powder compound C having the following formula in 400.4 g (yield 98%).

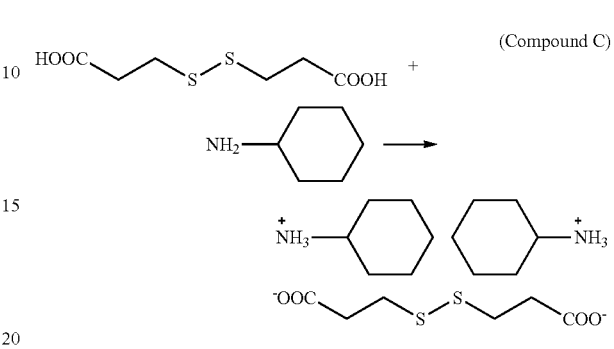

(Compound C)

$^1$HNMR (400 MHz, DMSO-$d_6$) δ in ppm: 1.1-1.2, 1.5, 1.7, 1.9, 2.3, 2.8, 2.9 Elementary analysis value (%): $C_{18}H_{36}N_2O_4S_2$ Calculated: C, 52.91; H, 8.88; N, 6.86; S, 15.69. Found: C, 52.83; H, 9.03; N, 6.84; S, 15.92.

Preparation Example 4

Synthesis of Amine Salt Compound of Disulfide D

In isopropyl alcohol 1000 g, dithiosalicyclic acid 306.4 g (1 mol) and t-butylamine 160.9 g (2.2 mol) were charged and reacted at room temperature for 30 minutes. After the end of the reaction, the product was filtered and was washed two times with acetone and dried to obtain a white powder compound D of the following formula in 445.3 g (yield 98%).

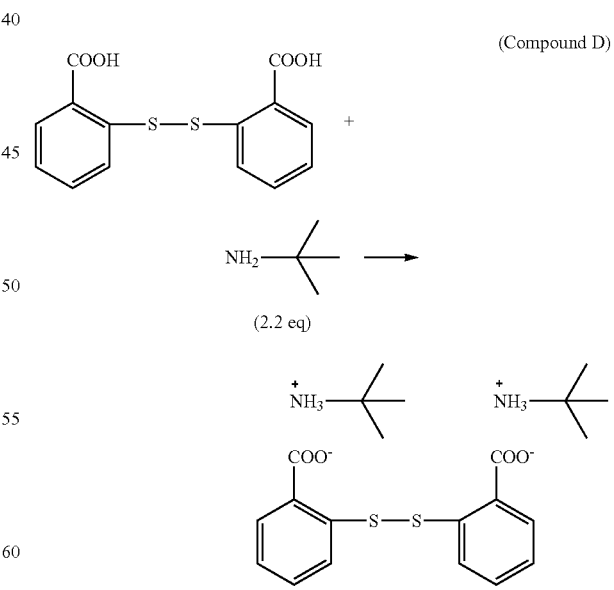

(Compound D)

$^1$H NMR (400 MHz, DMSO-$d_6$) δ in ppm: 1.3, 3.1, 7.1, 7.2, 7.5, 7.8 Elementary analysis value (%): $C_{22}H_{32}N_2O_4S_2$ Calculated: C, 58.38; H, 7.13; N, 6.19; S, 14.17. Found: C, 58.14; H, 7.26; N, 6.45; S, 14.58.

Preparation Example 5

Synthesis of Amine Salt Compound of Disulfide E

In methanol 1000 g, dithiosalicyclic acid 306.4 g (1 mol) and diisopropylamine 222.6 g (2.2 mol) were charged and reacted at room temperature for 30 minutes. After the end of the reaction, the methanol was removed in vacuo. The product was filtered and washed two times with acetone and dried to obtain a white powder compound 1 of the following formula in 501.2 g (yield 98.5%).

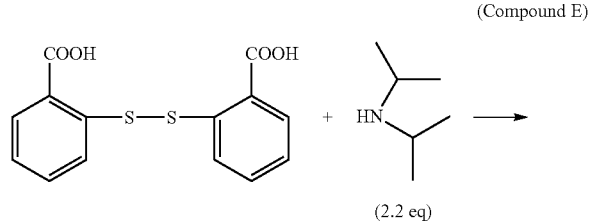

(Compound E)

(2.2 eq)

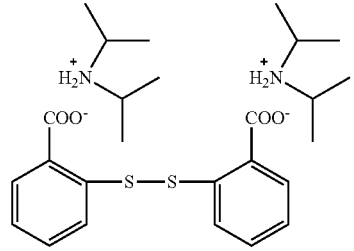

$^1$H NMR (400 MHz, DMSO-$d_6$) δ in ppm: 1.3, 3.2, 7.1, 7.2, 7.5, 7.8 Elementary analysis value (%): $C_{26}H_{40}N_2O_4S_2$ Calculated: C, 61.38; H, 7.93; N, 5.51; S, 12.61. Found: C, 60.86; H, 8.0; N, 5.63; S, 12.44.

Examples I-1 to I-7 and Comparative Examples I-1 to I-3

Preparation of Rubber Compositions

The formulation ingredients shown in the following Table I-1 were mixed in a 1.7 liter Banbury mixer for 5 minutes to make them uniform disperse and obtain the rubber compositions of the Examples and Comparative Examples. The rubber compositions of the Examples and Comparative Examples thus obtained were evaluated by the following test methods. The results are shown in Table I-1.

TABLE I-1

Formulation of Rubber Composition

| Ingredient | Comp. Ex. I-1 | Ex. I-1 | Ex. I-2 | Ex. I-3 | Ex. I-4 | Ex. I-5 | Comp. Ex. I-2 | Ex. I-6 | Ex. I-7 | Comp. Ex. I-3 |
|---|---|---|---|---|---|---|---|---|---|---|
| Natural rubber*[1] | 100 | 100 | 100 | 100 | 100 | 80 | — | — | — | 100 |
| SBR*[2] | — | — | — | — | — | 20 | — | — | — | — |
| Brominated butyl*[3] | — | — | — | — | — | — | 100 | 100 | 100 | — |
| Carbon black*[4] | 50 | 50 | 50 | 50 | 50 | 50 | 50 | 50 | 50 | 50 |
| Zinc oxide*[5] | 5 | 5 | 5 | 5 | 5 | 5 | 3 | 3 | 3 | 5 |
| Stearic acid*[6] | 1 | 1 | 1 | 1 | 1 | 1 | 2 | 2 | 2 | 1 |
| Antioxidant*[7] | 1 | 1 | 1 | 1 | 1 | 1 | — | — | — | 1 |
| Petroleum resin*[8] | — | — | — | — | — | — | 10 | 10 | 10 | — |
| Oil*[9] | — | — | — | — | — | — | 10 | 10 | 10 | — |
| Sulfur*[10] | 1.5 | 1.5 | 1.5 | 1.5 | 1.5 | 1.5 | 0.5 | — | 0.5 | 1.5 |
| Vulcanization accelerator CZ*[11] | 1 | — | — | — | — | — | — | — | — | — |
| Vulcanization accelerator DM*[12] | — | — | — | — | — | — | 1 | — | — | — |
| Compound A*[13] | — | 2 | — | — | — | 2 | — | 2.5 | 2.5 | — |
| Compound C*[13] | — | — | 2 | — | — | — | — | — | — | — |
| Compound D*[13] | — | — | — | 2 | — | — | — | — | — | — |
| Compound E*[13] | — | — | — | — | 2 | — | — | — | — | — |
| Dithiosalicylic acid*[14] | — | — | — | — | — | — | — | — | — | 2 |

Table I-1 notes
*[1]RSS#3
*[2]Nipol 1712 (made by Nippon Zeon)
*[3]Exxon Bromobutyl 2255 (made by Japan Butyl)
*[4]Diablack E (made by Mitsubishi Chemicals)
*[5]Zinc White #3 (made by Seido Chemical)
*[6]Beads Stearic Acid YR (made by NOF Corporation)
*[7]Nocrac 6C (made by Ouchi Shinko Chemical Industrial)
*[8]Hilets G-100X (made by Mitsui Chemicals)
*[9]Desolex No. 3 (made by Showa Shell Oil)
*[10]Goldflower brand sulfur powder (made by Tsurumi Chemical Industrial)
*[11]Noccelar CZ-G (N-cyclohexyl-2-benzothiazolyl sulfenamide) (made by Ouchi Shinko Chemical Industrial)
*[12]Noccelar DM-P (dibenzothiazyl disulfide) (made by Ouchi Shinko Chemical Industrial)
*[13]Compounds synthesized in Preparation Examples 1, 3, 4, and 5
*[14]Dithiosalicylic acid (made by Kanto Chemical)

Test Methods

Mooney Scorch

The unvulcanized rubber compositions were continuously measured for Mooney viscosity based on the provisions of JIS K6300-1994 using an L-rotor under conditions of a preheating time of 1 minute and a test temperature of 125° C. The minimum value of the Mooney viscosity was made $V_m$. Further, the Mooney scorch time until the Mooney viscosity rose 5 points from $V_m$ was measured. The results are shown in Table I-2. The Mooney scorch time is an indicator of the scorching. The longer the better.

Next, the rubber compositions obtained above were vulcanized at 150° C. for 30 minutes to prepare vulcanized sheets of 15 cm×15 cm×2 mm size. From the vulcanized sheets, JIS No. 3 dumbbell shaped test pieces were punched. According to JIS K6251, the modulus at the time of elongation of 300% (M300), tensile at break ($T_B$), and elongation at break ($E_B$) were found. Furthermore, according to JIS K6257, the M300 after aging at 80° C. for 96 hours was measured. The rate of change (%) of the value of the M300 after aging from the initial value of M300 was found by the following formula:

100×[(M300 after aging)−(M300 before aging)]/(M300 before aging)

The results are shown in Table I-2. The smaller the value of the rate of change, the better the heat aging resistance shown.

mixed in a 1.7 liter internal mixer for 5 minutes. When reaching 160° C., the result was discharged to obtain a master batch. The vulcanization accelerator and sulfur were mixed with this master batch by open rolls to obtain a rubber composition.

Next, the rubber composition obtained above was vulcanized in a predetermined mold at 150° C. for 30 minutes to prepare a test sample which was then measured by the test methods shown below for the physical properties of the vulcanized rubber. The results are shown in Table II-I.

Test Methods for Evaluation of Rubber Physical Properties

Elongation at break: According to JIS K 6251, a dumbbell No. 3 type sample was elongated at a speed of 500 mm/min to measure the elongation at break at 20° C. The results are shown indexed to the value of Comparative Example II-1 as 100. The larger this value, the higher the elongation shown.

Heat buildup: According to JIS K 6394, the tan δ at 20° C. was measured at an initial strain of 10%, an amplitude of 2% and a frequency of 20 Hz. The results are shown indexed to the value of Comparative Example II-1 as 100. The larger this value, the better the low heat buildup property shown.

TABLE I-2

Test Results

| | Comp. Ex. I-1 | Ex. I-1 | Ex. I-2 | Ex. I-3 | Ex. I-4 | Ex. I-5 | Comp. Ex. I-2 | Ex. I-6 | Ex. I-7 | Comp. Ex. I-3 |
|---|---|---|---|---|---|---|---|---|---|---|
| Scorch time (min) | 20.3 | 23.4 | 18.5 | 23.2 | 21.7 | 25.1 | 15.9 | >45 | 23.5 | 25.3 |
| $T_B$ (MPa) | 25.6 | 24.7 | 25.4 | 25.5 | 25.7 | 24.5 | 9.7 | 8.7 | 10.1 | 15.4 |
| $E_B$ (%) | 443 | 521 | 470 | 510 | 527 | 505 | 937 | 727 | 782 | 620 |
| M300 before aging (MPa) | 13.9 | 11.9 | 13.3 | 11.7 | 12.2 | 12.3 | 2.5 | 4.1 | 4.3 | 6.7 |
| M300 after aging (MPa) | 17.2 | 13.3 | 15.5 | 13.2 | 13.7 | 13.7 | 3.1 | 4.7 | 4.9 | 8.9 |
| Rate of change (%) | 23.7 | 11.8 | 16.5 | 12.8 | 12.3 | 11.4 | 24.0 | 14.6 | 14.0 | 32.8 |

Examples II-1 to II-4 and Comparative Examples II-1 to II-4

Preparation of Samples

In each formulation shown in Table II-I, the ingredients other than the vulcanization accelerator and sulfur were Bonding test: Based on ASTM D1871C, the peeling force necessary for peeling off a 25 mm width test piece at a speed of 500 mm/min was measured. The results are shown indexed to the value of Comparative Example II-1 as 100. The larger this value, the higher the bonding strength shown.

TABLE II-1

| | Comp. Ex. II-1 | Comp. Ex. II-2 | Comp. Ex. II-3 | Ex. II-1 | Ex. II-2 | Ex. II-3 | Comp. Ex. II-4 | Ex. II-4 |
|---|---|---|---|---|---|---|---|---|
| Formulation (parts by weight) | | | | | | | | |
| NR | 100 | 100 | 100 | 100 | 100 | 100 | 100 | 100 |
| CB | 50 | 50 | 50 | 50 | 50 | 50 | 50 | 50 |
| Zinc oxide | 10 | 10 | 10 | 10 | 10 | 10 | 10 | 10 |
| Stearic acid | 0.5 | 0.5 | 0.5 | 0.5 | 0.5 | 0.5 | 0.5 | 0.5 |
| Antioxidant | 2 | 2 | 2 | 2 | 2 | 2 | 2 | 2 |

TABLE II-1-continued

| | Comp. Ex. II-1 | Comp. Ex. II-2 | Comp. Ex. II-3 | Ex. II-1 | Ex. II-2 | Ex. II-3 | Comp. Ex. II-4 | Ex. II-4 |
|---|---|---|---|---|---|---|---|---|
| Cobalt salt | 1 | 1 | 1 | 1 | 1 | 1 | 1 | 1 |
| Sulfur | 9 | 9 | 9 | 9 | 9 | 9 | 9 | 9 |
| Vulcanization accelerator 1 | 1 | — | — | — | — | — | — | 0.5 |
| Vulcanization accelerator 2 | — | 1 | — | — | — | — | — | — |
| Vulcanization accelerator 3 | — | — | 0.08 | 0.2 | 1 | 4 | 5.5 | 0.5 |
| Physical properties | | | | | | | | |
| Elongation at break | 100 | 104 | 110 | 109 | 108 | 108 | 96 | 103 |
| Heat buildup | 100 | 94 | 98 | 100 | 101 | 102 | 103 | 100 |
| Bonding performance | 100 | 105 | 105 | 107 | 110 | 110 | 113 | 106 |

Table II-1 notes
NR: Natural rubber RSS #3
CB: Carbon Black Seast KH made by Tokai Carbon (iodine adsorption 90 cm$^3$/100 g, DBP absorption 119 × 10$^{-5}$ m$^3$/kg)
Zinc Oxide: Zinc Oxide #3 made by Seido Chemical Industrial
Stearic acid: Beads Stearic Acid made by NOF Corporation
Antioxidant (6D): Nocrac 224 made by Ouchi Shinko Chemical Industrial
Cobalt salt: Manobond made by Rhodia (Co content: 22%) (chemical formula: $(C_9H_{19}COO)_3B$)
Sulfur: Crystex HS OT 20 made by Akzo-Nobel
Vulcanization accelerator 1: Noccelar DZ-G made by Ouchi Shinko Chemical Industrial
Vulcanization accelerator 2: Noccelar DM-PO made by Ouchi Shinko Chemical Industrial
Vulcanization accelerator 3: Compound A synthesized by Preparation Example 1

INDUSTRIAL APPLICABILITY

As explained above, a rubber vulcanization use compounding agent including the amine salt compound of disulfide (I) of the present invention has a high vulcanization acceleration effect for diene-based rubbers and halogenated butyl rubber etc. and further acts as a vulcanization agent for halogenated butyl rubber. Further, the vulcanized rubber obtained by vulcanizing an unvulcanized rubber composition containing a rubber vulcanization use compounding agent containing an amine salt compound of a disulfide (I) of the present invention exhibits a higher heat aging resistance than one obtained from an unvulcanized rubber composition containing a conventional vulcanization agent and/or vulcanization accelerator. In the present invention, further, by using in the diene-based rubber an amine salt compound of a carboxylic acid group-containing disulfide as a vulcanization accelerator and using a specific carbon black and metal salt, it is possible to achieve both an improvement of the bonding performance of a tire with a metal belt and a low heat buildup property, and, therefore, this is useful as a rubber for belt coat and/or belt edge cushion or other rubber composition of a pneumatic tire.

The invention claimed is:

1. A compounding agent for rubber vulcanization comprising an amine salt compound of a carboxylic acid group-containing disulfide having the formula (I):

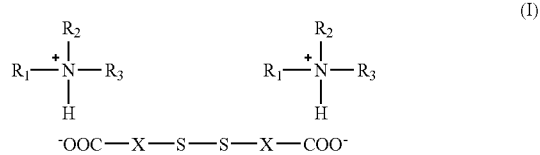

(I)

wherein $R_1$, $R_2$ and $R_3$ are independently hydrogen or a $C_1$-$C_{20}$ organic group which may have a heteroatom and/or substituent group and X is a $C_2$-$C_{20}$ organic group which may have a heteroatom and/or substituent group.

2. A compounding agent for rubber vulcanization as claimed in claim 1, wherein, in the above formula (I), the amine component is a primary or secondary amine.

3. A rubber vulcanization use compounding agent as claimed in claim 1, wherein, in the above formula (I), X is an aromatic group.

4. A method for producing an amine salt compound of a carboxylic acid group-containing disulfide having the formula (I) comprising:

reacting a thiol compound containing a carboxylic acid group having the formula (IV) and an amine having the formula (III):

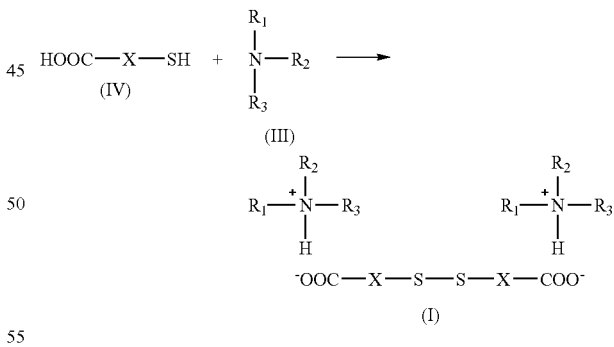

wherein $R_1$, $R_2$ and $R_3$ are independently hydrogen or a $C_1$-$C_{20}$ organic group which may have a heteroatom and/or a substituent group and X is $C_2$-$C_{20}$ organic group which may have a heteroatom and/or a substituent group.

5. A rubber composition comprising at least one unvulcanized rubber component selected from the group consisting of diene-based rubbers and halogenated rubber and a compounding agent for rubber vulcanization according to claim 1.

6. A pneumatic tire using, as a rubber for a belt coat and/or belt edge cushion, a rubber composition for a tire comprising:

(A) 100 parts by weight of a diene-based rubber containing at least 30 parts by weight or more of a natural rubber and/or polyisoprene rubber, (B) 0.1-5 parts by weight of an amine salt compound of a carboxylic acid group-containing disulfide having the formula (I):

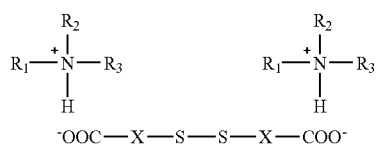

(I)

wherein $R_1$, $R_2$ and $R_3$ are independently hydrogen or a $C_1$-$C_{20}$ organic group which may have a heteroatom and/or substituent group and X is a $C_2$-$C_{20}$ organic group which may have a heteroatom and/or substituent group, (C) 20 to 80 parts by weight of carbon black having an iodine adsorption of 70 to 140 g/kg and a DBP absorption of 60 to $180\times10^{-5}$ m$^3$/kg and (D) 0.05 to 0.5 parts by weight, in terms of a metal content, of an organic metal salt.

7. A rubber vulcanization use compounding agent as claimed in claim 2, wherein, in the above formula (I), X is an aromatic group.

8. A rubber composition comprising at least one unvulcanized rubber component selected from the group consisting of diene-based rubbers and halogenated rubber and a compounding agent for rubber vulcanization according to claim 2.

9. A rubber composition comprising at least one unvulcanized rubber component selected from the group consisting of diene-based rubbers and halogenated rubber and a compounding agent for rubber vulcanization according to claim 3.

* * * * *